(12) United States Patent
Hsu et al.

(10) Patent No.: US 6,327,921 B1
(45) Date of Patent: Dec. 11, 2001

(54) NON-DESTRUCTIVE INSPECTIONS AND THE DISPLAY OF INSPECTION RESULTS

(75) Inventors: David K. Hsu; Daniel J. Barnard; John J. Peters; Nordica A. Hudelson, all of Ames, IA (US)

(73) Assignee: Iowa State University, Ames, IA (US)

( * ) Notice: Subject to any disclaimer, the term of this patent is extended or adjusted under 35 U.S.C. 154(b) by 0 days.

(21) Appl. No.: 09/517,957

(22) Filed: Mar. 3, 2000

(51) Int. Cl.$^7$ .................................................. B29C 47/92
(52) U.S. Cl. .............................................................. 73/866.5
(58) Field of Search ........................... 73/12.01, 12.04, 73/12.09, 12.11–12.14, 865.8, 866.5, 598, 606, 607, 633; 324/228, 237, 238, 240

(56) References Cited

U.S. PATENT DOCUMENTS

| | | |
|---|---|---|
| 3,805,795 | 4/1974 | Denniston et al. . |
| 4,542,639 | 9/1985 | Cawley et al. . |
| 5,048,320 | 9/1991 | Mitsuhashi et al. . |
| 5,345,514 * | 9/1994 | Mahdavieh et al. .................. 324/240 |
| 5,686,675 * | 11/1997 | Barton .................................. 73/866.5 |

OTHER PUBLICATIONS

Adams et al., "Nondestructive Inspection of Composite Structures by Low Velocity Impact," *Review of Prog. In Quantitative NDE*, 1986, vol. 5, Plenum Press, New York, pp. 1253–1258.

Adams et al., "Low–Velocity Impact Inspection of Bonded Structures," *Imech E*, 1986, pp. 139–142.

Cawley et al., "The Mechanics of the Coin–Tap Method of Non–Destructive Testing," *J. Sound and Vibration*, 1988, 122(2):299–316.

Cawley et al., "Sensitivity of the Coin–Tap Method of Nondestructive Testing," *Materials Evaluation*, May 1989, 47:558–563.

Georgeson et al., "Electronic Tap Hammer for Composite Damage Assessment," SPIE Proceedings, (Nondestructive Evaluation of Aging Aircraft, Airports and Aerospace Hardware—ed. by Rempt and Broz) 1996, 2945:328–338.

Gieske, "Evaluation of Scanners for C–Scan Imaging for Nondestructive Inspection of Aircraft," Nov. 1997, NDT-net—vol. 2, No. 11.

Mobile Automated Scanner (MAUS®) III/IV Brochure, undated, admitted to be prior art.

Woodpecker WP632 Brochure, Mitsui Engineering & Shipbuilding Co., Ltd., not dated.

* cited by examiner

*Primary Examiner*—Robert Raevis
(74) *Attorney, Agent, or Firm*—Fish & Richardson, P.C., P.A.

(57) ABSTRACT

A non-destructive inspection system makes use of a template that is put on a structure to be inspected to provide an image-based display of inspection results. The template, an example of which is a grid, defines locations on the structure from which inspection data are obtained. A portable display device, an example of which is a laptop computer, with information about the template receives information pertaining to inspection data obtained from locations defined by the template and displays inspection results in an image-based format that corresponds to the template. An example of such a system uses "tap test" non-destructive inspection techniques and provides an image-based display of a plurality of structural stiffness measures, each stiffness measure calculated from a measure of impact duration for a "tap".

12 Claims, 5 Drawing Sheets

NON-DESTRUCTIVE INSPECTIONS AND THE DISPLAY OF INSPECTION RESULTS

This work was supported in part by the Federal Aviation Administration under Delivery Order DTFA03-98-F-IA016.

TECHNICAL FIELD

This invention relates to non-destructive inspection techniques, and more particularly to an image-based display of inspection results. In addition, an aspect of the invention relates to "tap test" non-destructive inspections and the display of "tap test" inspection results.

BACKGROUND

A non-destructive inspection allows an inspector to gain information about underlying structure and potential defects within that structure without having to destroy the structure. Non-destructive techniques are used to identify both service- and manufacturing-related flaws and damage. Some examples of non-destructive techniques are "tap tests," eddy currents, and ultrasonics. A tap test has applicability to inspecting aircraft structures, and is well suited for inspecting composite and metal honeycomb structures. To perform a tap test, a tap test probe, like probe 20 shown in FIG. 1, is tapped against a structure under inspection. Generally, the less stiff a tapped structure is, the duller the sound of the tap, and also the longer the probe remains in contact with the tapped structure. Contact time—also called impact duration ($\tau$)—is related to the stiffness of the tapped structure based on a grounded-spring mechanical model, which yields the following equation:

$$\tau = \pi(m_T/k)^{1/2} \text{ or } k = m_T(\pi/\tau)^2$$

where $m_T$ and k are respectively the mass of the tap test probe and local stiffness (or spring constant) of the structure being inspected.

One known tap test device for inspecting aircraft structures is the Rapid Damage Detection Device ($RD^3$) built and tested by the Boeing Defense & Space Group, and described in Georgeson et al., "Electronic tap hammer for composite damage assessment," SPIE, vol 2945, pp. 328–38. The $RD^3$ is a hand-held device that consists of a hammer containing an accelerometer in the hammer's head. The hammer is connected by a cable through its handle to a hand-held module containing electronics and a liquid crystal digital display (LCD). The accelerometer in the head of the hammer translates a force-time pulse for each tap into a voltage. Georgeson et al. note that the width of this pulse is sensitive to local stiffness. The electronics in the hand-held module takes a measurement of the width of the pulse at a pre-set level of 4.8 volts. The measured pulse width is displayed as a number on the LCD display. After each hammer tap, the display resets and shows a new value. Another tap test inspection device is the Woodpecker WP632 Tapping Exfoliation Detector developed by Mitsui Engineering & Shipbuilding Co., Ltd (see also U.S. Pat. No. 5,048,320). The WP632 also processes the force-time pulse and provides a measure of contact time. The WP632 compares the measured contact time with a reference value and provides an indication of the inspection result by way of light emitting diodes that light up when an abnormality is detected. The WP632 may be connected to a separate monitoring unit for showing and memorizing measured contact time values. The monitoring unit can also transmit this data to a personal computer.

Although the $RD^3$ and Woodpecker WP632 devices both display a measure of the width of the force-time pulse, and that width is related to stiffness by the equation identified above, neither device calculates or displays a measure of stiffness itself. Also, Cawley and Adams discuss possible ways the force-time history and/or frequency spectra of an impact may be compared to the force-time history and/or frequency spectra of a reference impact in the article "Sensitivity of the Coin-Tap Method of Nondestructive Testing," Materials Evaluation, pp. 558–63 (May 1989). Cawley and Adams note that obvious candidates are comparisons of peak force, impact duration (that is, the width of the force-time history pulse), and rate of decrease of force, but comment that all these possibilities have serious drawbacks, and in particular note that a test based on impact duration would tend to be unreliable. Cawley and Adams then describe another method, which involves obtaining the frequency spectrum of the force pulse with the use of a Fourier-transform microchip. The spectrum is analyzed to come up with a measure that approximates the degree of high-frequency force. Cawley and Adams note that impacts over defects have lower high frequency force than impacts over good areas.

Two-dimensional "C-scan" images have also been used to display non-destructive inspection results. C-scans are two-dimensional images produced by digitizing point-by-point signal variations of an interrogating sensor while it is scanned over a surface. Such displays have been provided using a conventional C-scan apparatus placed on the structure to be inspected. The C-scan apparatus carries an inspection probe across the structure taking inspection data at various points. Multiple inspection data points are thus obtained, along with corresponding location information for each datum obtained. This information is sent to a video display device where inspection results are displayed in a format that shows the inspection results arranged to correspond to the locations of the structure from which the data were obtained. A C-scan display such as this is described as having been used with a tap test device called the "Tapometer," in the article by Adams, Allen & Cawley, "Nondestructive Inspection of Composite Structures by Low-velocity Impact," in QNDE, vol. 5, 1986, Plenum Press, New York.

C-scan images have diagnostic benefits because of being able to distinguish easily between an actual defect and normal stiffness variations due to, for example, internal support structures. However, the need for a C-scan apparatus imposes portability limitations that prevent its use in many cases. For example, when inspecting an aircraft structure in a maintenance environment, it is rarely an option to remove from the aircraft the structure needed to be inspected and take it to a laboratory to perform the inspection. The same holds true for other structures typically inspected by non-destructive techniques, for example, pipelines. The C-scan apparatus also may cause the structure being tested to be scratched, either by the frame of the C-scan apparatus itself when securing the frame to the structure to be inspected or when removing it, or by the C-scan apparatus scratching the structure when moving an inspection probe from one inspection point to another. Moreover, for curved structures such as the leading edge of aircraft wings, a C-scan apparatus, with its large rigid frame, cannot be used.

SUMMARY

The invention, in one aspect, is a highly portable system for conducting non-destructive inspections and displaying the inspection results in a quantitative and image-based manner. A template—for example, a transparent sheet on which a grid is printed or a projected image of a grid—is put on a structure to be inspected. The template defines a plurality of locations from which inspection data are obtained. A display device with information about the template receives information pertaining to inspection data from locations defined by the template and displays inspection results in an image-based format that corresponds to the template. In another aspect, the invention provides to a user, for a tap test, a displayed measure of stiffness or stiffness reduction. The inventors have found that stiffness, or percentage reduction in stiffness, calculated from an accurate measure of impact duration time obtained from a force-time pulse produced by a tap test, provides a reliable and useable inspection result measure.

In one embodiment, the non-destructive inspection technique is a tap test, and the system includes a tap test probe, a pulse-width measurement circuit, and a conventional computer that is programmed to process inspection data and provide a display of inspection results. In preferred embodiments, a portable laptop computer can be used. The probe produces an electrical pulse indicative of the force-time history of a tap. The pulse-width measurement circuit determines a measure of impact duration for a tap and provides a digital signal indicative of that measure to the portable computer. The pulse-width measurement circuit may include an amplifier to ensure the entire width of the force-time pulse is measured, and hence a reliable measure of impact duration is obtained. The portable computer computes, for each measure of impact duration, a measure of stiffness. The portable computer may also, and preferably, compute, using a baseline measure, a percentage measure of stiffness reduction. The graphical display may be of either the impact duration measures or the stiffness measures such as the percentage of stiffness reduction. This tap test embodiment is effective for inspecting composite structures and metal honeycomb sandwich structures, such as those used on aircraft.

The invention affords one or more of the following advantages. The invention provides for the performance of tap tests in non-laboratory environments in a quantitative and image-based manner, which results in two-dimensional images showing local stiffness. The template is a simple, convenient and low-cost way to encode the tap test data, and to instruct the display device (a computer with software) to properly position the tap test data and generate the two-dimensional images of impact duration and local stiffness in the computer, without using complicated positioning and encoding devices. The concept of using a template is applicable not only to tap tests, but to other non-destructive inspection techniques as well. The system is highly portable and usable and thus ideal for use in aircraft maintenance environments. Portability is owed in part to the use of a template instead of a relatively non-portable C-scan apparatus. Also, the system is designed so that it may be entirely battery-operated, which too furthers its portability. In addition, an image-based display, provided in real time where the inspection is being performed, adds diagnostic value to the inspection technique, and also makes the inspection quicker and easier. Also, the preferred pulse-width measurement circuit disclosed below provides an accurate measure of impact duration, and also is low-cost solution which avoids more costly analog-to-digital converters and Fourier transform microelectronics.

The details of embodiments illustrating the invention are set forth in the accompanying drawings and the description below. Other features, objects, and advantages of the invention will be apparent from the description and drawings, and from the claims.

DESCRIPTION OF DRAWINGS

Like reference symbols in the various drawings indicate like elements.

DETAILED DESCRIPTION

Figure 1:
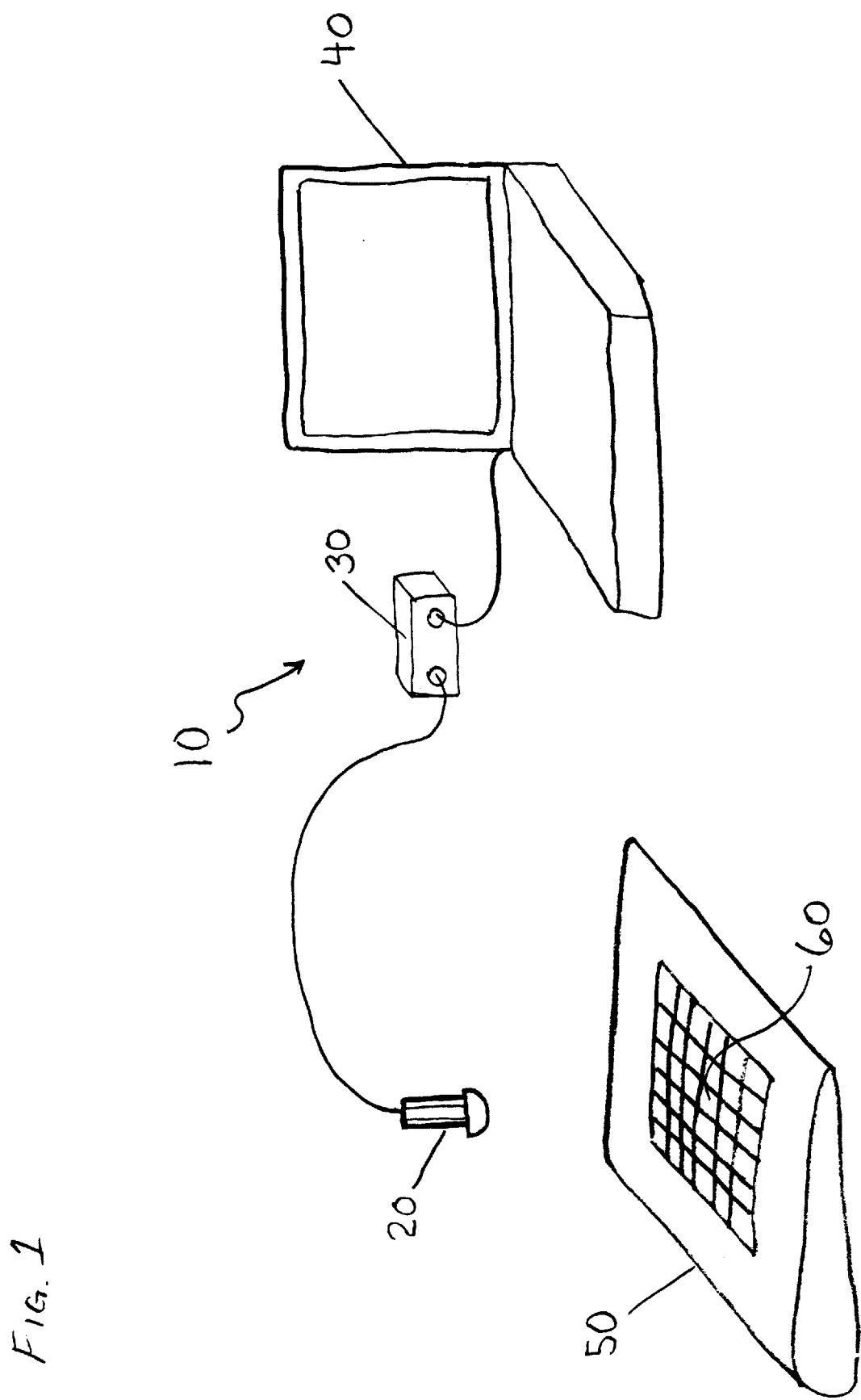
FIG. 1 is a pictorial figure of a non-destructive inspection and display system built in accordance with the invention, along with a structure to be inspected.

A non-destructive inspection and display system 10 in accordance with an embodiment of the invention, shown in FIG. 1, includes a tap test probe 20, a pulse-width measurement circuit 30, and a portable laptop computer 40. The system 10 is used to inspect the structural integrity of a structure, for example, a flap 50 of an aircraft wing, and then displays the results of that inspection. A template in the form of a grid printed on a sheet of thin transparent material 60 is placed on the structure 50 over the area to be inspected. In operation, briefly, the probe 20 is tapped against each square of the grid in a specified sequence. Each tap produces a voltage pulse that is received by circuit 30. Circuit 30 processes each pulse to determine a measure of impact duration for the tap, and generates a digital signal indicative of impact duration. The computer 40 receives the digital signal of impact duration for each tap in succession, computes a measure of stiffness from each impact duration measure, and provides a display of inspection results for the area of the grid, in an image-based format that corresponds to the grid and its individual sections.

The tap test probe 20 includes a piezoelectric accelerometer with a hemispherical brass or steel tip attached to an end of it. The tip of the probe 20 is tapped against the structure 50. The probe 20 may be tapped by hand, much like in a "coin tap" test practiced by the aircraft inspection industry. This is referred to below as the manual version of inspection. Alternatively, the probe 20 may be installed into a mechanical module that includes a friction wheel, several gears, and a cam, which together move the probe 20 up and down as the module is moved across the surface of the structure 50, thus causing periodic taps. This is referred to below as the mechanical module version of inspection. Such a mechanical module is shown in Provisional U.S. Patent Application, Hsu el at. of the Iowa State Research Foundation, Inc., "Magnetic Cam Action," filed Jan. 29, 2000, and incorporated by reference herein.

Figure 2:
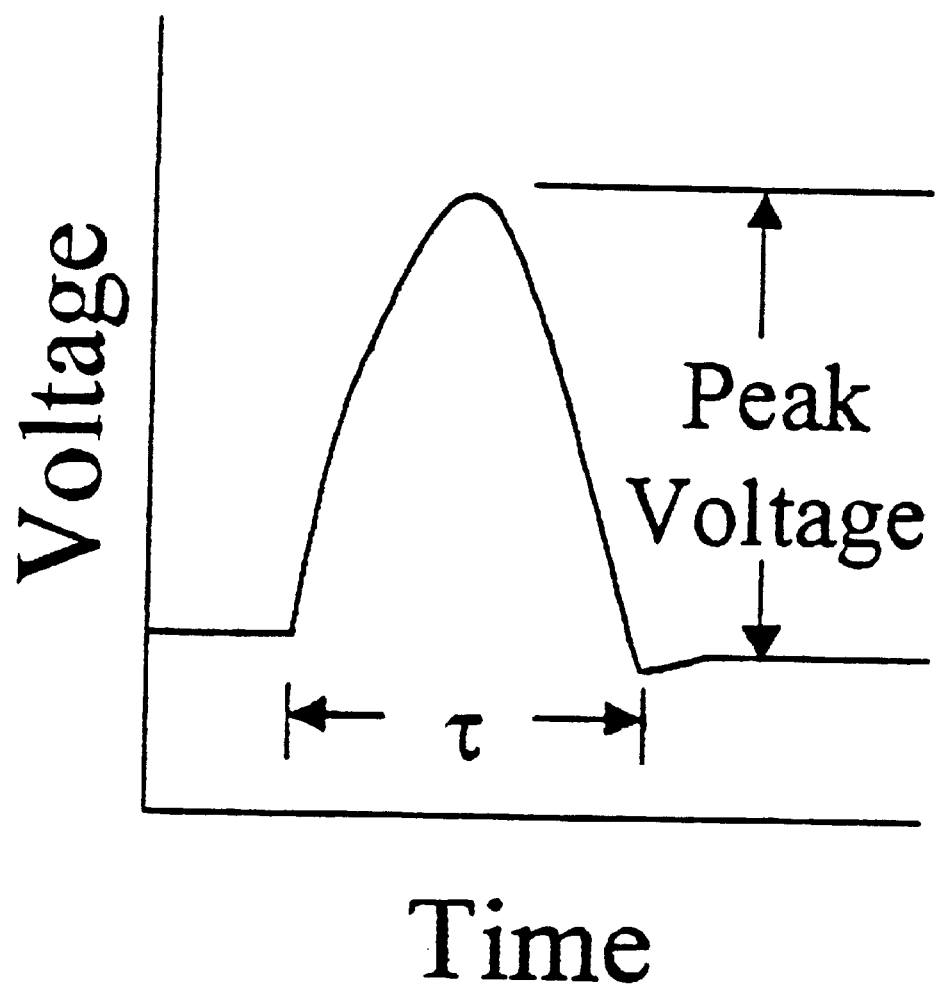
FIG. 2 is a graph showing an example voltage pulse produced by a probe used in the system shown in FIG. 1.

When the probe 20 is tapped, generally, the stiffer the structure 50 is, the shorter the time the tip of the probe 20 remains in contact with the structure 50. Each tap produces a voltage pulse output from the probe 20 to the circuit 30. An example of such a voltage pulse is shown in FIG. 2. The voltage pulse represents the force-time history of the impact. This pulse is usually followed by a small undershoot where the output voltage goes slightly negative and then recovers toward zero. The width of the pulse ($\tau$) represent impact duration. The amplitude of the pulse (labeled "voltage peak") depends on the force of the tap. When a tap is made of a good region of a structure, the pulse amplitude is high and the pulse duration (τ) is short. In contrast, when the tap is made over a damaged region, for example, over a crushed core or skin-to-core disbond, the pulse amplitude is lower and the pulse width is greater.

If the force of the tap is increased, the amplitude of the pulse increases, but the width of the pulse (impact duration, τ) remains relatively constant. For example, the inventors found that on a Boeing 747 trailing edge flap (having a 2.5" thick structure of fiberglass honeycomb with glass fiber reinforced plastic (GFRP)skins), when the tap force was increased to a level that produced a voltage pulse five times as high, the impact duration only increased by approximately five percent. The same behavior was found for other structures typically inspected using a tap test method. Thus, the impact duration (τ) is for all practical purposes tap force independent. In addition as discussed above, stiffness of the inspected structure is related to impact duration (τ) based on a grounded-spring mechanical model; hence the following equation:

$$\tau = \pi (m_T/k)^{1/2} \text{ or } k = m_T(\pi/\tau)^2$$

where $m_T$ and k are respectively the mass of the probe 20 and local stiffness (spring constant) of the structure 50 being inspected. Stiffness (k), therefore, can be deduced from measured impact duration (τ), as it is inversely proportional to the square of impact duration.

Because impact duration is insensitive to the force of the tap, the manual version of inspection described above, with its inevitable human variability in tap force, works adequately. Compared to the mechanical module version of tapping also described above, however, the manual version can be more tedious. Therefore, in some applications it is preferable to use the mechanical module version. Nevertheless, the manual version may still be preferable to the mechanical module version in some applications, for example, on curved surfaces such as leading edges of aircraft wings. In particular, the mechanical version may be less adaptive to surface variations.

Figure 3:
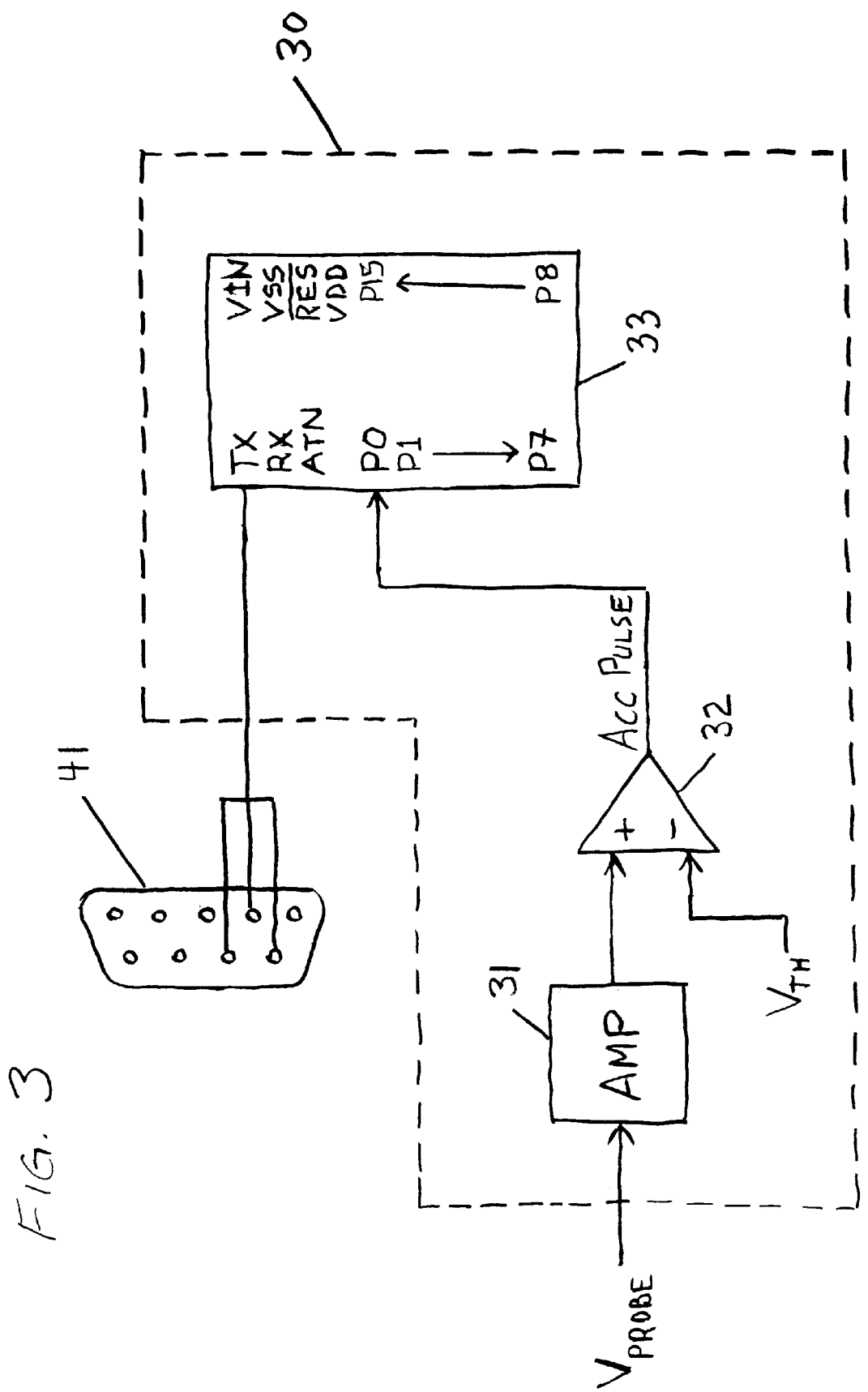
FIG. 3 is a hybrid block and schematic diagram of a circuit used in the system shown in FIG. 1.

The pulse-width measurement circuit 30, shown in FIG. 3, is battery-operated (battery not shown). The circuit 30 receives, from the probe 20, the voltage ($V_{PROBE}$), which contains the pulses representing the force-time histories of taps. The circuit 30 measures the impact duration (τ) for each pulse and provides those measures in digital format to the portable computer 40 (FIG. 1) at its serial port connection 41 (FIG. 3). To do this, first an adjustable-gain amplifier 31 amplifies the voltage $V_{PROBE}$. A comparator 32 then receives the amplified $V_{PROBE}$ and compares that voltage to an adjustable threshold voltage ($V_{TH}$). If the amplified $V_{PROBE}$ is less than $V_T$, the output of comparator 32 is "off," and if greater than, it is "on." A microcontroller 33 receives the comparator 32 output (labeled "Acc Pulse"). In the example circuit 30 shown in FIG. 3, the microcontroller 33 is a BASIC Stamp II made by Parallax, Inc. The microcontroller 33 is programmed so that when "Acc Pulse" first goes "on," an internal clock is started, and then when the "Acc Pulse" subsequently goes "off," the clock is stopped. The time that "Acc Pulse" is "on" is the measure of impact duration (τ), which the microcontroller 33 outputs, digitally, at pin "TX" to the serial connector 41. The box in which circuit 30 resides has user-adjustable controls (not shown) by which to adjust the gain of amplifier 31 and the threshold voltage ($V_{TH}$) for comparator 32. The idea is to have the gain set so that when the pulse at $V_{PROBE}$ begins, the voltage rises vertically instead of gradually, and when the pulse ends, the voltage drops to zero instantaneously. The voltage threshold ($V_{TH}$) is set, optimally, just above the noise threshold. With the amplifier 31 gain and compare threshold ($V_{TH}$) so adjusted, the amplifier 31 and comparator 32 produce a pulse at "Acc Pulse" whose time duration is an accurate reflection of impact duration (τ). As such, it is ensured that the pulse-width measurement circuit 30 will provide an accurate measure of impact duration.

It will be appreciated that the pulse-width measurement circuit 30 is a simple and inexpensive solution by which to obtain a digital measure of impact duration. The microcontroller 33, for example, can be purchased at a cost of about $40, thus making the total cost for the circuit 30 approximately $55. An alternative to this approach is to use an analog-to-digital (A/D) conversion card for the computer 40, although such an approach would add significant additional cost. However, the A/D card solution may be preferable where an A/D card is already available and perhaps used for other purposes.

Before proceeding to describe the computer 40 used in the system 10, it is helpful to first obtain an understanding of the template. The basic idea behind using a template is to define with it a plurality of locations from which individual inspection data will be obtained. For example, if the template is in the form of a grid as shown in FIG. 1, each square of the grid may define a separate location from which one inspection datum will be obtained. The computer 40 is programmed with the geometries of the template, so that as inspection data are obtained in a specified sequence from the locations defined by the template, the computer 40 is able to provide a display of inspection results in an image-based format that corresponds to the geometry of the template and the plurality of inspection locations defined by the template.

The template shown in FIG. 1 is a grid and is printed on a sheet of thin transparent material 60. Mylar material of 0.003" thickness is suitable, and was found to have negligible effect on impact duration (approximately 3–4% difference from the impact duration without the Mylar material placed over the structure 50). The transparent sheet 60 is placed on the area of the structure 50 to be inspected, and may be secured in place by tape, for example. The grid template, shown in FIG. 1, serves well with the manual version of inspection. With such a template, a user takes the probe 20 in hand and taps it within each square of the grid, thereby obtaining an inspection datum for each square of the grid. Of course it need not be the case that the entire grid be used, if, for example, a standard grid template is larger than the area that needs to be inspected. An example grid may be one with ¾" squares. This yields 256 inspection locations per square foot, or in other words, 16 rows of 16 inspection locations. For the mechanical module version of the inspection, a template with parallel lines serves the purpose, which could be the same grid template, as it has parallel lines, or alternatively a template with only parallel lines. An example of a parallel line template would be one where the parallel lines are spaced ¾" apart. The mechanical module carrying the probe 20 is moved along each line of the template. As this is done, the mechanical module performs a tap of the probe 20 repeatedly after the module travels a specified distance, which may be, for example. ¾".

Other template designs may also be used, depending upon the application. For example, a specific aircraft or a specific component may have a template design that is tailored for the specific of the area to be inspected. Thus, computer 40 may store template information for different applications, and permit user selection of the grid that is being used. Also, the sheet on which the template is printed need not be transparent, though the transparency aids in the positioning of the template so that a particular grid section may be placed over a particular flaw area, or to relate the position of some flaw or damage revealed in a tap test to certain landmarks, for example, the edges of splices or rows of rivets. Also, a template with cut out locations may alternatively be created, such that there is no intermediate material between the probe 20 and the structure 50. It is also not necessary to use a sheet of material with a grid printed on it. For example, it may also be practical in some instances to use a projector to project the template onto the surface of the test structure, or it may be possible to mark the template directly on the structure 50, for example, with an erasable marker or "grease pencil," or if the structure is going to be painted, with any marker that will be painted over.

Figure 4:
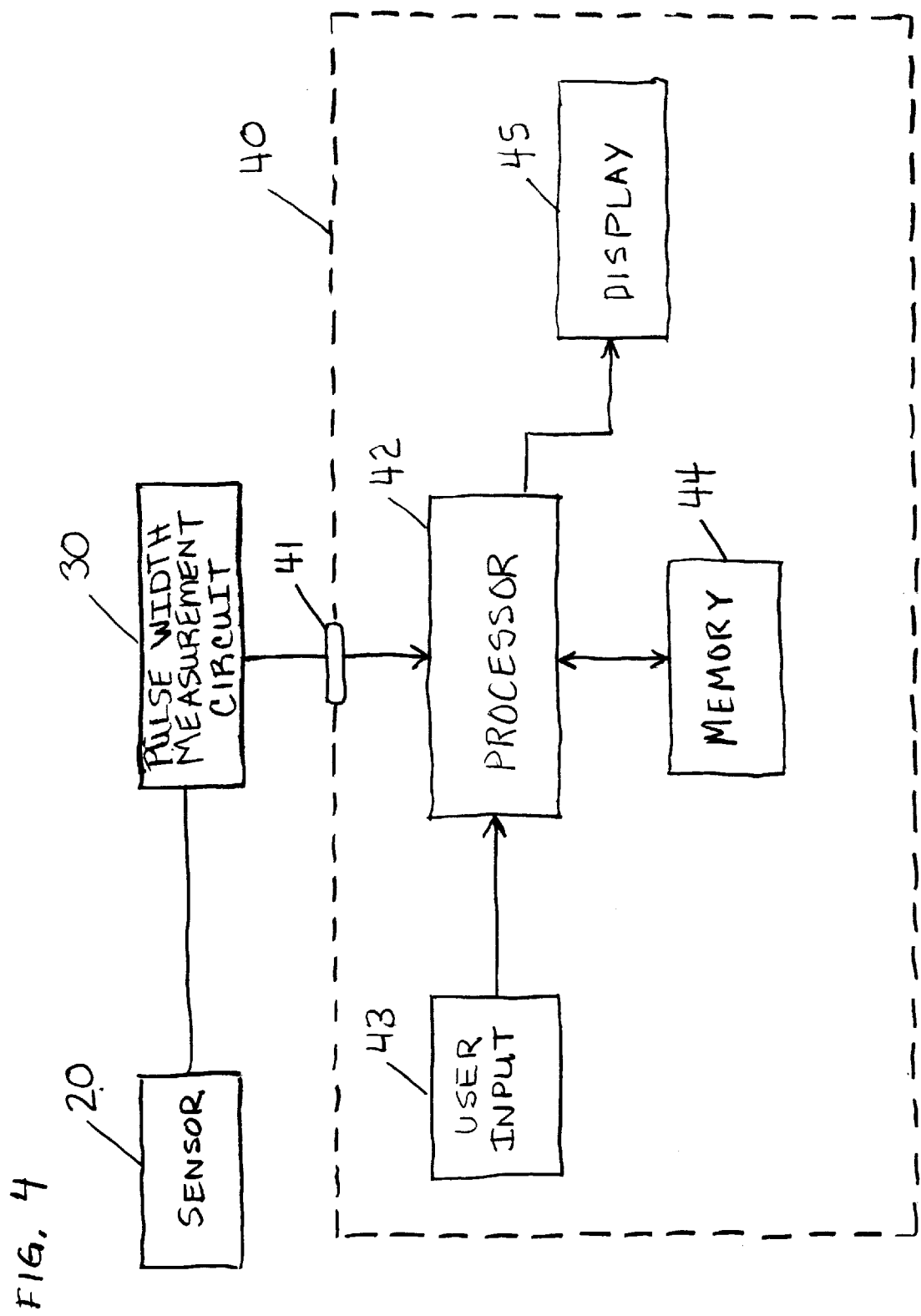
FIG. 4 is a block diagram of the system shown in FIG. 1, showing in particular blocks within a computer used in the system shown in FIG. 1.

Finally, the computer 40, shown in more detail in FIG. 4, in conventional fashion includes a processor 42, user input 43 including a keyboard and mouse, memory 44, and a video display 45. The computer 40 could be a portable laptop computer, or alternatively, it could be a personal digital assistant (PDA) or other hand-held computer with display capability, or a dedicated device with functionality customized for the testing application. The computer 40 performs several functions in the context of the invention, including allowing the user to set up for an inspection, acquiring impact duration data from circuit 30, processing the data to calculate stiffness, and providing an image-based display of inspection results that corresponds to the template. These functions are described in more detail below. The software to perform these functions may be written, for example, in Microsoft® Visual Basic for Applications, and may make use of a commercially available spreadsheet program, such as Microsoft® Excel, for spreadsheet and display functions. This software program will be referred to below as the inspection software program.

Performing an inspection begins with the user identifying the area on structure 50 to be inspected and positioning on that structure an appropriate template. Once this is done, the user, with the user input 42, makes an appropriate selection to begin operation of the inspection software program. The user is then prompted, on display 45, to enter parameters needed to perform the inspection. For example, the user is prompted to enter parameters that pertain to the probe 20, for example, the mass, size and material of the tip, and the model and serial numbers of the accelerometer. The user is also prompted to enter information about the type of structure to be tested. For example, the user may indicate a particular aircraft or surface type. The mass of the probe tip is used in the calculation of stiffness from a measure of impact duration measure, as indicated by the above equation. The other parameters are entered for documentation purposes.

Next, the user is prompted to enter parameters identifying the template. In one example where a grid template is used, the number of rows and columns is entered, along with the size of each square of the grid. For example, a 30×20 grid with ½" squares defines a 15"×10" test area. Other examples depend on the geometry of the template used. Preferably, the user need not actually enter the parameters to identify the template, as the desired parameter may be a default parameter, or may be identical to a parameter used in, and saved from, a previous inspection. Preferably in the latter case, the user only need recall a previous inspection and use the set up parameters from that inspection. Computer 40 may be programmed to present the user with a table or menu of templates for user selection.

Once set up is complete, the user is prompted to begin the process of gathering inspection data. This begins with a prompt for the user to perform five taps on the structure 50 from a defect—or damage—free region. This serves to verify that the system is working properly and establishes a baseline to which later-collected inspection data are compared. Once the five taps have been done, the user is prompted to begin taking inspection data in a specified sequence at various locations determined by the template. For example, in the manual version of the inspection using the grid template, a tap is performed at each square defined by the grid, starting with the square in the upper left and proceeding through each row from left to right until the lower right corner of the template is reached. As an aid to the user, the computer 40 may sound a tone every fifth tap, and the template could have every fifth square shaded, so the user would know that a box has not been duplicated or skipped. In addition, the computer 40 may sound a different tone to signal the end of a row, and yet another, and preferably longer, tone to signal the end of the entire grid. Because many environments in which the system is used are noisy, an ear microphone may be used to ensure the user hears the tones. The mechanical module version using a parallel line template is done similarly. The mechanical module is placed on the top horizontal line at the line's left end and is moved to the line's right end. In moving the mechanical module along the line the mechanical module causes the probe 20 to tap every ¾", for example. After the top line is complete, each successive line is done left to right, for example, until the bottom right corner of the template is reached.

As each tap is done, circuit 30 determines the impact duration, as described above, and sends the digital signal indicative of impact duration to the serial port 41 of computer 40. The inspection software program includes instructions that provide for the monitoring of serial port 41 such that, upon receipt of an impact duration measure, the processor 42 takes it and from it calculates a measure of stiffness using the equation identified above. In addition, the processor 42 may also calculate a percentage measure of stiffness reduction using a baseline measure calculated by averaging the five baseline taps mentioned above. Each impact duration measure and corresponding stiffness measure is stored in memory 44 in a manner that maintains the correspondence of the impact duration measure and stiffness measure to the template position to which the data relate.

As the collection of inspection data progresses, a display of the impact duration time may be immediately provided on a grid displayed on display 45. As mentioned above, the display feature may be implemented using a commercially available spreadsheet program, such as Microsoft® Excel. The display corresponds to the template used. This is made possible because the computer 40 is programmed, during set up, with information about the template. Therefore, a continually updated display of inspection results is immediately provided as the inspection progresses. By way of an example, where a grid template is used consisting of 16 rows and 16 columns of squares, the display 45 will likewise show a grid of 16 rows and 16 columns of squares, albeit on a smaller scale. The display of the inspection results includes a selected quantitative measure (that is, a number)—impact duration, stiffness, or stiffness reduction—that is displayed at the appropriate position of the template that is displayed on display 45. Also, the template location on display 45, in addition to displaying the quantitative measure, may also be shaded in color-coded fashion to indicate a range in which the inspection result measure falls, with the entire range of measures spanning several colors proceeding through a spectrum of colors.

Once the last grid section has been tapped, the inspection software program causes all stiffness measures to be automatically examined for points that are out-of-range. For example, these may be very low values of impact duration (less than 50 microseconds or so due to noise at the leading edge of the pulse). If an out-of-range measure is detected, the user is prompted with an option to re-tap the appropriate grid section or to average the data using nearest neighbors. When all of the out-of-range stiffness measures have been re-tapped or otherwise addressed, the user is then prompted querying whether the user would like to tap any particular grid section again. If so, the user selects the template location using user input 43 (FIG. 4), and re-taps the corresponding location on structure 50 accordingly. It will be appreciated that the ability of the user-immediately seeing the inspection results in an image-based format allows the user to immediately identify anomalous data that may be the result of a faulty tap, and re-test the location. The re-tapping of template locations continues until the user no longer wishes to re-tap any locations. The inspection is now complete, and the final display is provided on display 45. The user has the option of storing the inspection results in a results data file, which may be called up at a later time and re-displayed.

Figure 5:
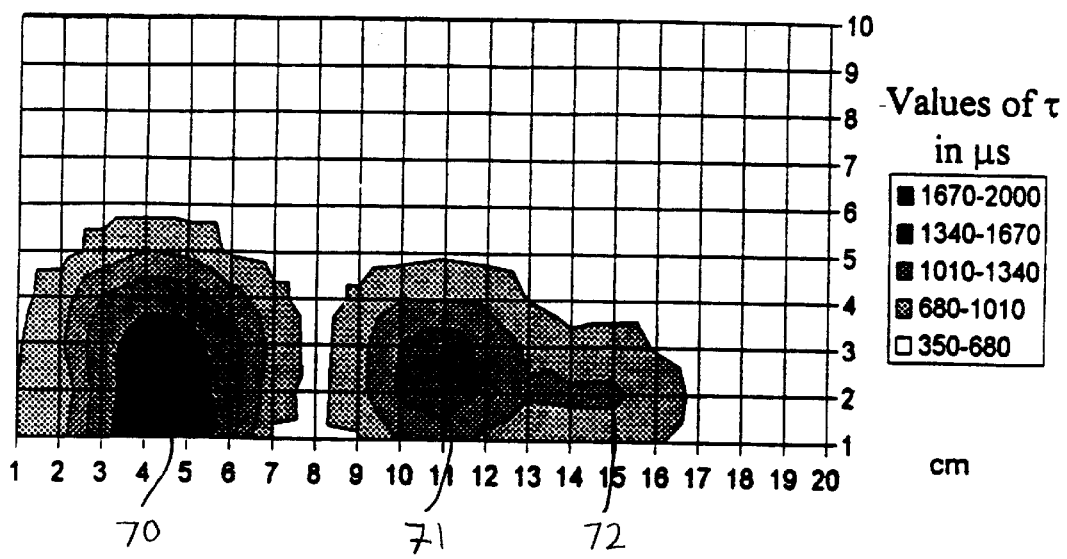
FIGS. 5 and 6 are examples displays of inspection results produced by the system shown in FIG. 1.
Figure 6:
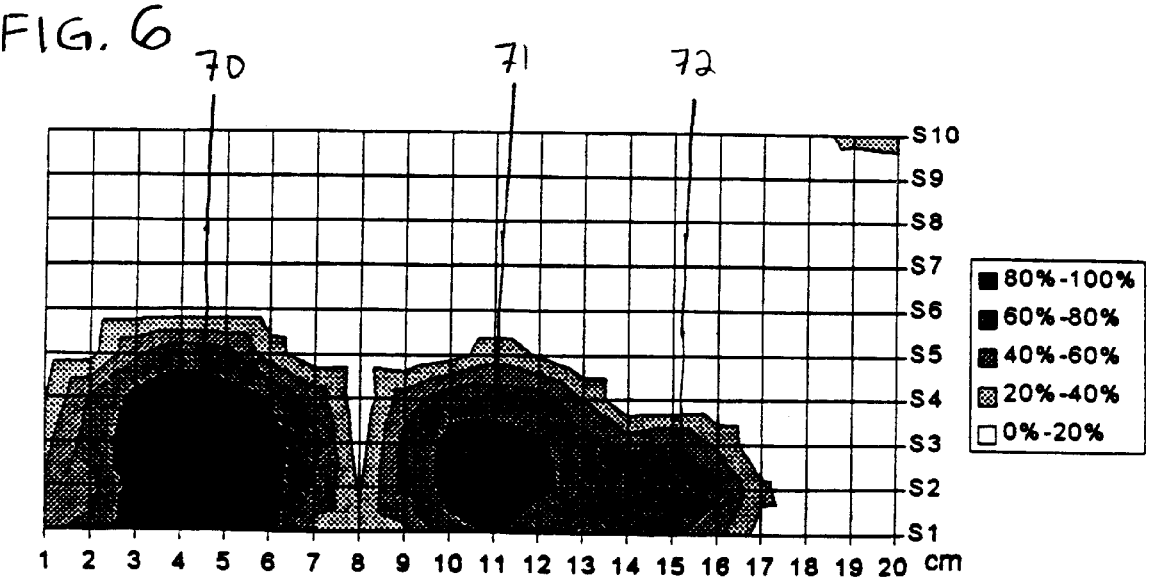

It is possible, using the Excel spreadsheet program, to also display the inspection results in an interpolated format. This is done in a similar color-coded format, and the user may select the desired inspection result measure to display—impact duration, stiffness, or percentage reduction in stiffness. Examples of such displays are shown in FIGS. 5 and 6. The displays show the results of a tap test inspection performed on a retired Boeing 747 trailing edge flap having a 2.5" thick structure of fiberglass honeycomb with GFRP skins. On a section of the flap, three impact damages were induced with drop weights. The first damage site, corresponding to location 70 on the displays of FIGS. 5 and 6, was hit by a 1.5" diameter steel ball dropped from a height of 23 feet, with an incident kinetic energy of 15 J. The second damage site, corresponding to location 71, was induced by the same steel ball, but dropped from a height of 15 feet, with an incident kinetic energy of 9.8 J. The third damage site, corresponding to location 72, was induced by a 1" diameter steel ball dropped from a height of 15 feet, with an incident kinetic energy of 2.9 J. The structure was inspected using the manual version described above with a 1 cm×1 cm grid pattern. The resulting image of impact duration $\tau$ is shown in FIG. 5. The figure shows the most severe damage on the left and the least severe damage on the right, not quite resolved from the intermediate damage in the middle. FIG. 6 shows a display of stiffness measures from the same inspection, with the percent measures indicating the percent reduction in spring stiffness, k. An image of the stiffness variation is more closely related to the mechanical properties of a structure and therefore more useful in the evaluation of the severity of flaw or damage.

It will be appreciated that the system 10 is highly portable and entirely battery-operated, and thus ideal for maintenance environments for aircraft. In addition, the system 10 avoids the use of scanners that are much less portable, and in some cases cannot even be used to inspect some structures, for example, the curved leading edge of a wing. Also, although an embodiment using a tap test type of non-destructive inspection technique is described above, the portable image-based display aspect of the invention has applicability to other non-destructive inspection techniques where similar inspection environment constraints are posed. Two examples of other non-destructive inspection techniques are eddy current and ultrasonic inspections. However, unlike the tap test method where each data point consists of an easily identifiable event (i.e., the pulse) which serves to trigger the pulse-width measuring circuit 30 and hence indicate to the computer 40 that an inspection datum has been taken, other non-destructive inspection techniques do not have such easily identifiable inspection points. Nevertheless, it may be possible to include in these applications some type of user-activated mechanism to trigger the collection of a data point and indicate to the rest of the system that that has happened. Also, although the testing of an aircraft structure is identified above, it should not be taken that the invention is limited thereby. Other examples of tap test applications include pipelines, space structures such as an antenna, the antenna of the airborne warning and control system (AWACS), the hull of racing sailboats, superstructures on naval ships like the mast that cover the radar. It will be understood that various other modifications may be made without departing from the spirit and scope of the invention. Accordingly, other embodiments are within the scope of the following claims.

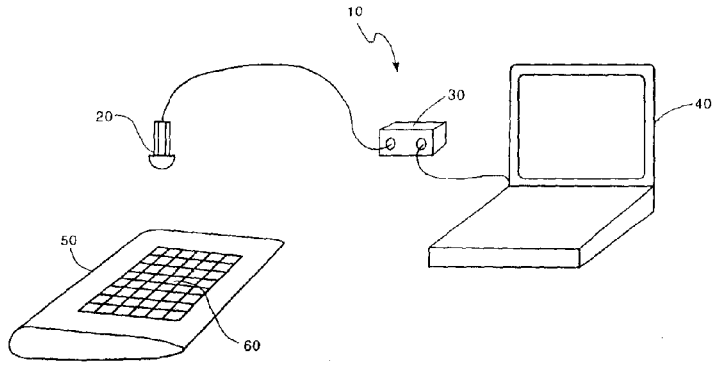

What is claimed is:

1. A system for performing a non-destructive inspection of a structure and displaying the results, comprising:
    a probe for obtaining non-destructive inspection data at a plurality of locations on the structure, the locations indicated by a template on the structure;
    a processor for processing each of the inspection data obtained by the probe to create for each datum an inspection result measure; and
    a display device for displaying the plurality of inspection result measures in an image-based format that corresponds to the template.

2. The system of claim 1 wherein the probe is a tap test probe.

3. The system of claim 2 wherein the inspection result measures are measures of impact duration determined from the inspection data.

4. The system of claim 2 wherein the inspection result measures are measures of stiffness calculated using a grounded-spring mechanical model from measures of impact duration determined from the inspection data and the mass of the probe.

5. The system of claim 4 wherein the only feature of a tap test inspection datum that is used in the calculation of a measure of stiffness is a measure of impact duration determined from the inspection data.

6. The system of claim 1 wherein the template is a grid.

7. The system of claim 1 wherein the template is a plurality of lines parallel to one another.

8. A system for performing a tap test inspection of a structure and displaying the results of the structure, comprising:
    a tap test probe produces an electrical pulse indicative of the force-time history of impact between the probe and the structure;
    a circuit for receiving the electrical pulse from the probe, determining a measure of impact duration, and producing a digital signal indicative of the impact duration measure;
    a portable computer for receiving from the circuit a plurality of digital signals indicative of impact duration measures, the plurality of impact duration measure digital signals corresponding to tap test inspection data obtained from the structure at a plurality of locations defined by a template put on the structure, the portable computer including a display for displaying results of the tap test inspection in an image-based format that corresponds to the template.

9. The system of claim 8 wherein the results of the tap test inspection are the plurality of impact duration measures.

10. The system of claim 8 wherein the results of the tap test inspection are a plurality of measures of stiffness calculated by the portable computer from the plurality of impact duration measures.

11. The system of claim 8 wherein the template is a grid defining a plurality of grid squares, and wherein the plurality of grid squares define the locations from which the inspection data are obtained.

12. The system of claim 8 wherein the template is a plurality of parallel lines, and wherein periodic points along the lines comprise the plurality of locations from which the inspection data are obtained.

* * * * *

UNITED STATES PATENT AND TRADEMARK OFFICE
CERTIFICATE OF CORRECTION

PATENT NO. : 6,327,921 B1 Page 1 of 7
DATED : December 11, 2001
INVENTOR(S) : Daniel J. Barnard. Nordica A. Hudelson, Dr. David K. Hsu and John J. Peters It is certified that error appears in the above-identified patent and that said Letters Patent is hereby corrected as shown below:

Title page,
Showing an illustrative figure, should be deleted and substitute therefor the attached title page.

Drawings,
Please delete the drawings consisting of Figures 1-6, and insert the formal drawings consisting of Figures 1-6 therefore.

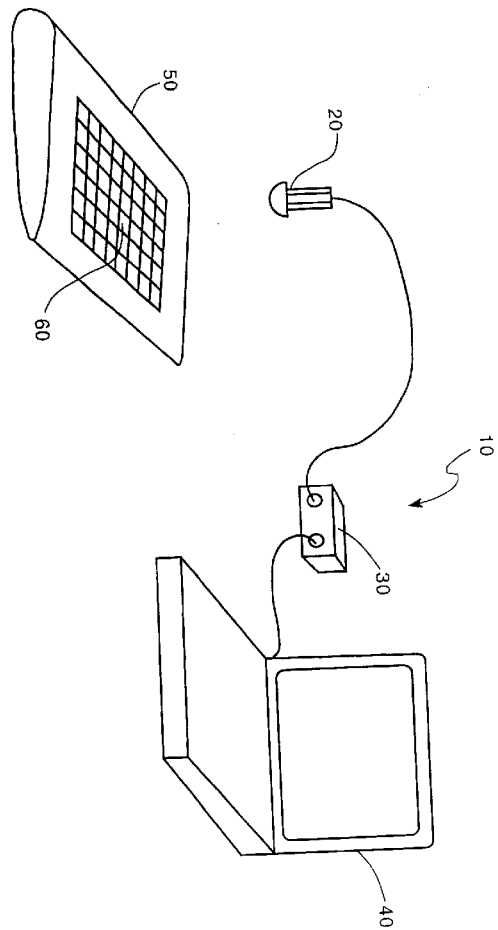

UNITED STATES PATENT AND TRADEMARK OFFICE
CERTIFICATE OF CORRECTION

PATENT NO. : 6,327,921 B1
DATED : December 11, 2001
INVENTOR(S) : Daniel J. Barnard, Nordica A. Hudelson, Dr. David K. Hsu and John J. Peters It is certified that error appears in the above-identified patent and that said Letters Patent is hereby corrected as shown below:

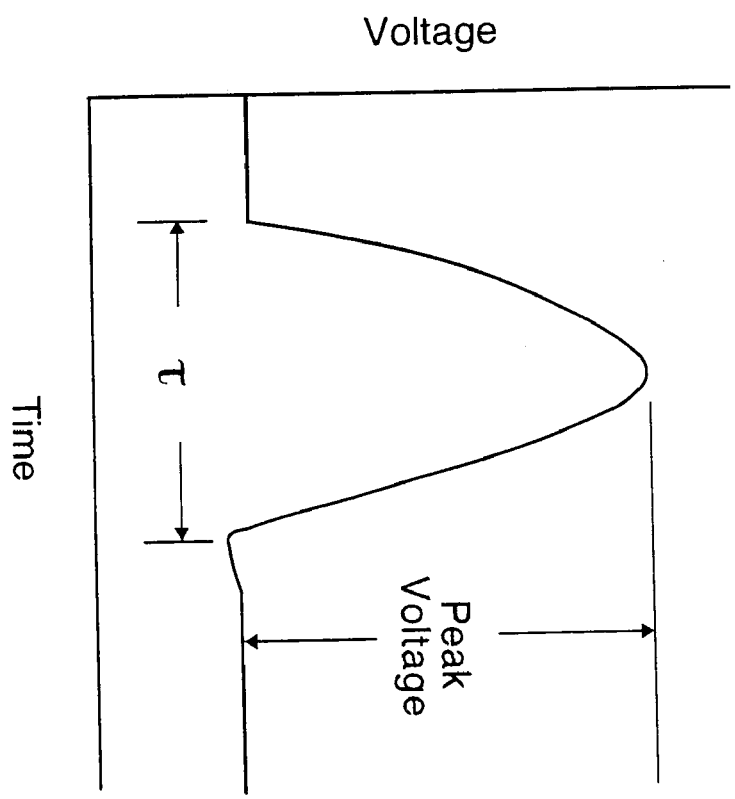

FIG. 2

UNITED STATES PATENT AND TRADEMARK OFFICE
CERTIFICATE OF CORRECTION

PATENT NO.    : 6,327,921 B1
DATED         : December 11, 2001
INVENTOR(S)   : Daniel J. Barnard, Nordica A. Hudelson, Dr. David K. Hsu and John J. Peters It is certified that error appears in the above-identified patent and that said Letters Patent is hereby corrected as shown below:

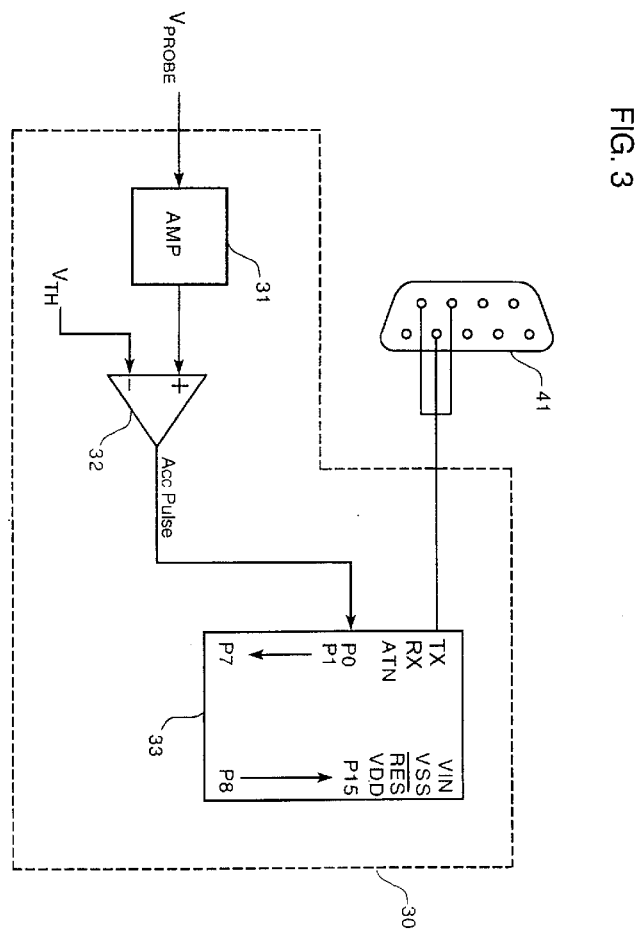

FIG. 3

UNITED STATES PATENT AND TRADEMARK OFFICE
CERTIFICATE OF CORRECTION

PATENT NO. : 6,327,921 B1
DATED : December 11, 2001
INVENTOR(S) : Daniel J. Barnard, Nordica A. Hudelson, Dr. David K. Hsu and John J. Peters It is certified that error appears in the above-identified patent and that said Letters Patent is hereby corrected as shown below:

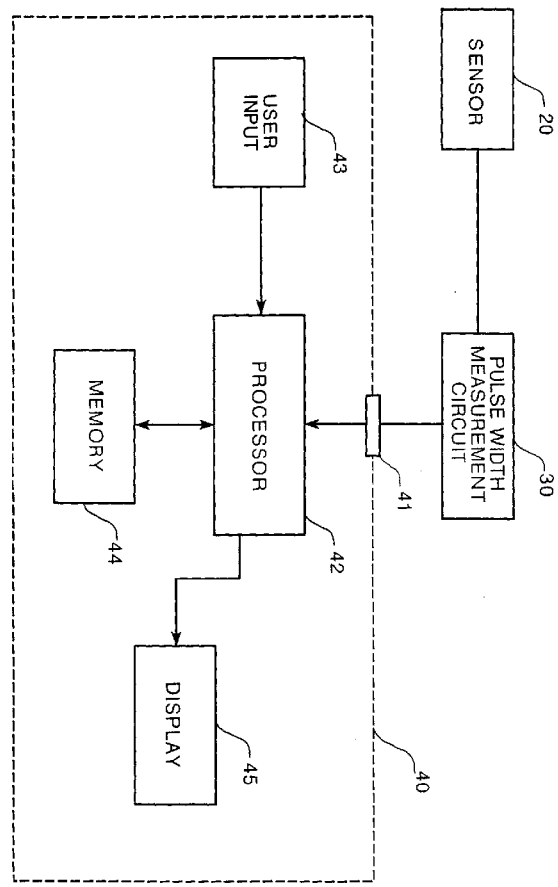

FIG. 4

UNITED STATES PATENT AND TRADEMARK OFFICE
CERTIFICATE OF CORRECTION

PATENT NO. : 6,327,921 B1  Page 5 of 7
DATED : December 11, 2001
INVENTOR(S) : Daniel J. Barnard, Nordica A. Hudelson, Dr. David K. Hsu and John J. Peters It is certified that error appears in the above-identified patent and that said Letters Patent is hereby corrected as shown below:

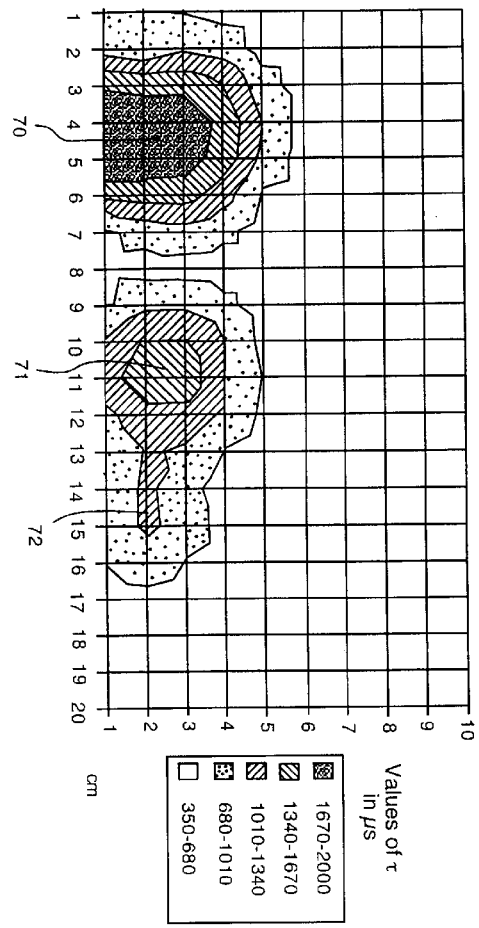

UNITED STATES PATENT AND TRADEMARK OFFICE
CERTIFICATE OF CORRECTION

PATENT NO.      : 6,327,921 B1
DATED           : December 11, 2001
INVENTOR(S)     : Daniel J. Barnard, Nordica A. Hudelson, Dr. David K. Hsu and John J. Peters It is certified that error appears in the above-identified patent and that said Letters Patent is hereby corrected as shown below:

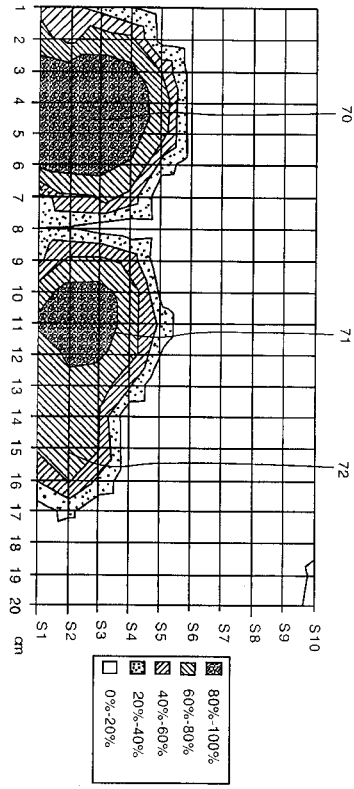

Signed and Sealed this

Ninth Day of July, 2002

*Attest:*

*Attesting Officer*

JAMES E. ROGAN
*Director of the United States Patent and Trademark Office*

(12) United States Patent
Hsu et al.

(10) Patent No.: US 6,327,921 B1
(45) Date of Patent: Dec. 11, 2001

(54) NON-DESTRUCTIVE INSPECTIONS AND THE DISPLAY OF INSPECTION RESULTS

(75) Inventors: David K. Hsu; Daniel J. Barnard; John J. Peters; Nordica A. Hudelson, all of Ames, IA (US)

(73) Assignee: Iowa State University, Ames, IA (US)

(*) Notice: Subject to any disclaimer, the term of this patent is extended or adjusted under 35 U.S.C. 154(b) by 0 days.

(21) Appl. No.: 09/517,957

(22) Filed: Mar. 3, 2000

(51) Int. Cl.$^7$ ................................................. B29C 47/92
(52) U.S. Cl. .................................................... 73/866.5
(58) Field of Search ........................... 73/12.01, 12.04, 73/12.09, 12.11–12.14, 865.8, 866.5, 598, 606, 607, 633; 324/228, 237, 238, 240

(56) References Cited

U.S. PATENT DOCUMENTS

| | | |
|---|---|---|
| 3,805,795 | 4/1974 | Denniston et al. . |
| 4,542,639 | 9/1985 | Cawley et al. . |
| 5,048,320 | 9/1991 | Mitsuhashi et al. . |
| 5,345,514 * | 9/1994 | Mahdavieh et al. ............... 324/240 |
| 5,686,675 * | 11/1997 | Barton ............................... 73/866.5 |

OTHER PUBLICATIONS

Adams et al., "Nondestructive Inspection of Composite Structures by Low Velocity Impact," *Review of Prog. In Quantitative NDE*, 1986, vol. 5, Plenum Press, New York, pp. 1253–1258.

Adams et al., "Low–Velocity Impact Inspection of Bonded Structures," *Imech E*, 1986, pp. 139–142.

Cawley et al., "The Mechanics of the Coin–Tap Method of Non–Destructive Testing," *J. Sound and Vibration*, 1988, 122(2):299–316.

Cawley et al., "Sensitivity of the Coin–Tap Method of Nondestructive Testing," *Materials Evaluation*, May 1989, 47:558–563.

Georgeson et al., "Electronic Tap Hammer for Composite Damage Assessment," SPIE Proceedings, (Nondestructive Evaluation of Aging Aircraft, Airports and Aerospace Hardware—ed. by Rempt and Broz) 1996, 2945:328–338.

Gieske, "Evaluation of Scanners for C–Scan Imaging for Nondestructive Inspection of Aircraft," Nov. 1997, NDT-net—vol. 2, No. 11.

Mobile Automated Scanner (MAUS®) III/IV Brochure, undated, admitted to be prior art.

Woodpecker WP632 Brochure, Mitsui Engineering & Shipbuilding Co., Ltd., not dated.

* cited by examiner

*Primary Examiner*—Robert Raevis
(74) *Attorney, Agent, or Firm*—Fish & Richardson, P.C., P.A.

(57) ABSTRACT

A non-destructive inspection system makes use of a template that is put on a structure to be inspected to provide an image-based display of inspection results. The template, an example of which is a grid, defines locations on the structure from which inspection data are obtained. A portable display device, an example of which is a laptop computer, with information about the template receives information pertaining to inspection data obtained from locations defined by the template and displays inspection results in an image-based format that corresponds to the template. An example of such a system uses "tap test" non-destructive inspection techniques and provides an image-based display of a plurality of structural stiffness measures, each stiffness measure calculated from a measure of impact duration for a "tap".

12 Claims, 5 Drawing Sheets